United States Patent [19]
Chambers et al.

[11] Patent Number: 5,882,660
[45] Date of Patent: Mar. 16, 1999

[54] PERSONAL CARE COMPOSITION

[75] Inventors: John George Chambers; Graham Andrew Turner, both of Wirral, United Kingdom

[73] Assignee: Lever Brothers Company, Division of Conopco, Inc., New York, N.Y.

[21] Appl. No.: 794,719

[22] Filed: Feb. 3, 1997

[30] Foreign Application Priority Data

Feb. 2, 1996 [GB] United Kingdom .................. 9602111

[51] Int. Cl.⁶ ..................................... A61K 7/48
[52] U.S. Cl. ......................... 424/401; 514/844; 514/845; 514/846
[58] Field of Search ..................... 424/401; 514/844–846

[56] References Cited

U.S. PATENT DOCUMENTS

| | | | |
|---|---|---|---|
| 4,189,465 | 2/1980 | Rosenthal | 424/10 |
| 4,760,096 | 7/1988 | Sakai et al. | 514/847 |
| 4,778,783 | 10/1988 | Gondra et al. | 512/2 |
| 5,079,003 | 1/1992 | Scaffidi | 424/401 |
| 5,476,660 | 12/1995 | Somasundaran et al. | 424/401 |

FOREIGN PATENT DOCUMENTS

| | | |
|---|---|---|
| 015030 | 9/1980 | European Pat. Off. . |
| 028457 | 5/1981 | European Pat. Off. . |
| 308190 | 3/1989 | European Pat. Off. . |
| 366070 | 5/1990 | European Pat. Off. . |
| 556957 | 8/1993 | European Pat. Off. . |
| 1052704 | 12/1966 | United Kingdom . |
| 2047563 | 12/1980 | United Kingdom . |
| 2178312 | 2/1987 | United Kingdom . |
| 86/06275 | 11/1986 | WIPO . |
| 90/01323 | 2/1990 | WIPO . |
| 94/00127 | 1/1994 | WIPO . |
| 96/12469 | 5/1996 | WIPO . |

OTHER PUBLICATIONS

WPI Abstract Acc. No. 84–053793/09 and JP 59013707 A.

*Primary Examiner*—Jyothsna Venkat
*Attorney, Agent, or Firm*—Ronald A. Koatz

[57] ABSTRACT

A personal care composition in the form of an aqueous liquid comprises:

i) a lipid composition comprising two components D and E, where D is a molecule having one long hydrocarbon chain and a hydrophillic head group and E is a material which comprises at least one of a compound selected from 3β-sterol; squalane; squalane; saponins or sapogenins of the plant steroid or triterpenoid type; di and tri terpenes such as phytol, retinol and amyrin; and mixtures thereof, wherein D and E are respectively present at levels within the range 0.1 to 10 wt % and 0.2 a to 12 wt % based on the total composition;

ii) a surface active agent selected from anionic, nonionic, cationic, zwitterionic, amphoteric surface active agents, soap and mixtures thereof; and iii) a deposition aid; and the composition is substantially free of a molecule having at least two hydrocarbon chains and a polar head group which satisfies the relationship $$0.5 < \frac{V}{a_o I_c} \leq 1.0: \quad (I)$$

where
V is the volume of the hydrocarbon chains
$I_c$ is the critical length of the hydrocarbon chains and
$a_o$ is the optimum area of the polar head group.

The composition may in the form of for example a shower gel or facial cleanser which is temporarily applied to the skin before being removed such as wiping or rinsing it from the skin.

1 Claim, No Drawings

PERSONAL CARE COMPOSITION

The invention relates to a personal care composition in liquid or gel form suitable for personal washing. In particular, it is concerned with compositions, intended for washing and/or cleansing of the human skin, which prevent or ameliorate skin dryness, skin wrinkling, chapping and ageing.

It is generally understood that ceramides present within the intercellular lipid lamellae of the stratum corneum play an important role in the production and maintenance of the water permeability barrier of the skin. Ceramides, or substances closely related to them, have been disclosed as components of skin care composition. In particular, Kao Corporation in GB 2178312 and GB 2213723 discloses the use of natural ceramides extracted from skin in products for topical application. Also, Kao Corporation in EP 227994 and EP 282816 discloses the use of synthetic ceramides, which are similar to their natural counterparts found in skin.

It is also known that, in addition to ceramides, the lipid lamellae comprises sterol and fatty acids (N. Y. Schurer, P. M. Elias (1991) Adv Lip Res A 27-56 Acad Press).

It is believed that one of the causes of skin drying and ageing is a reduction in the amount of lipid contained within intercellular lipid lamella of the stratum corneum. It has been shown in Intermolecular and Surface Forces, (1985) Jacob N Isrealachvili, ed Acad Press, Chapter 16 entitled "Aggregation of Amphiphilic Molecules into Micelles, Bilayers, Vesicles and Biological Membranes" that suitable lipids for forming a bilayer are those having a polar head group and at least two hydrocarbon chains, such that there exists a clearly defined relationship between the volume occupied by the hydrocarbon chains and the optimum area occupied by the polar head group. This relationship is that:

$$0.5 < \frac{V}{a_o l_c} \leq 1.0: \quad (I)$$

where

V is the volume of the hydrocarbon chains $l_c$ is the critical length of the hydrocarbon chains $a_o$ is the optimum area of the polar head group.

EP-A-556 957 discloses compositions comprising (a) a molecule having at least two hydrocarbon chains and a polar head group which satisfies the relationship (I) above such as ceramides, (b) long chain fatty acids and a third component (c), for example squalene, which is capable of assisting and stabilising lipid bilayers formed in the composition and where the ratio of a:b:c is from 1:1.5 to 6.0:1.1 to 8.0 respectively. The disclosed compositions are intended for topical application to the human, hair, skin or nails. In particular they are "leave-on" products which are intended to be permanently applied to the hair, skin or nails.

WO 94/00127 also discloses three component lipid compositions which may be combined with an aqueous phase containing a surface active agent. Like EP-A-557 957, the compositions disclosed in this reference are intended as "leave-on" products.

The aforementioned prior art compositions are intended as "leave-on" products which are not wiped or rinsed off. A disadvantage with such compositions is that they may leave the skin feeling oily.

There is a continued need for products which are able to successfully replace depleted lipids and alternative compositions such as cleansing compositions which are only temporarily applied to the skin before being removed. In our copending patent application PCT/EP95/03967 personal care compositions comprising a lipid composition comprising molecule A) which satisfies relationship (I) above such as a sucrose ester; B) long chain fatty acids, and a third component C) such as cholesterol which is capable of assisting and stabilising lipid bilayers formed in the composition can be formulated with surfactants to form a personal care composition which is intended to be temporarily applied to the skin before being rinsed or wiped off are disclosed. These personal care compositions provide an effective control of water loss and/or repair of damage to the water barrier layer in the stratum corneum.

We have now found that it is possible to formulate compositions in the absence of the aforementioned component A whilst still maintaining the beneficial properties of the prior art compositions i.e. effective control of water loss and/or repair of damage to the water barrier layer in the stratum corneum.

Thus, according to the invention there is provided a personal care composition in the form of an aqueous liquid comprising i) a lipid composition comprising two components D and E, where D is a molecule having one long hydrocarbon chain and a hydrophillic head group and E is a material which comprises at least one of a compound selected from 3β-sterol; squalene; squalane; saponins or sapogenins of the plant steroid or triterpenoid type; di and tri terpenes such as phytol, retinol and amyrin; and mixtures thereof, wherein D and E are respectively present at levels within the range 0.1 to 10 wt % and 0.2 to 12 wt % based on the total composition;

ii) a surface active agent selected from anionic, nonionic, cationic, zwitterionic, amphoteric surface active agents, soap and mixtures thereof; and iii) a deposition aid; and the composition is substantially free of a molecule having at least two hydrocarbon chains and a polar head group which satisfies the relationship $$0.5 < \frac{V}{a_o l_c} \leq 1.0: \quad (I)$$

where

V is the volume of the hydrocarbon chains $l_c$ is the critical length of the hydrocarbon chains and $a_o$ is the optimum area of the polar head group.

Furthermore, the invention also provides a personal care composition in the form of an aqueous liquid comprising i) a lipid composition comprising two components D and E, where D is a molecule having one long hydrocarbon chain and a hydrophillic head group and E is a material which comprises at least one of a compound selected from 3β-sterol; squalene; squalane; saponins or sapogenins of the plant steroid or triterpenoid type; di and tri terpenes such as phytol, retinol and amyrin; and mixtures thereof, wherein D and E are respectively present at levels within the range 0.1 to 10 wt % and 0.2 to 12 wt % based on the total composition;

ii) a surface active agent selected from anionic, nonionic, cationic, zwitterionic, amphoteric surface active agents, soap and mixtures thereof; and iii) a deposition aid; and is substantially free of ceramides; pseudoceramides; phospholipids; glycolipids having a structure of two or more acyl or alkyl long chains suitably containing from 14 to 50 carbon atoms each, attached to a polar group; specific esters of polyethylene glycol; polyglycerol-n-x oleate (CAS 9007-48-1); sorbitan dioleate (CAS 29116-98-1); sorbitan sesquioleate (CAS 8007-43-0); long chain alkyl other versions of phospholipids and glycolipids.

By substantially free is meant that this component, if present, in the compositions of the invention is only present in trace amounts introduced by way of impurities in the other constituents of the composition.

Component D

Component D is a molecule having one long hydrocarbon chain and a hydrophilic head group. Preferred materials are straight-chained mono carboxylic acids having 8 to 24 carbon atoms, straight-chained fatty alcohols having 8 to 24 carbon atoms, sugar esters, alkylated sugars and mixtures thereof.

Most preferably the materials are selected from straight chained substantially saturated (i.e. at least 85% saturated) mono-carboxylic fatty acids having 8 to 20 carbon atoms and straight chained saturated fatty alcohols having 8 to 20 carbon atoms. Mixtures of these fatty acids or fatty alcohols may also be used.

Particularly preferred materials are stearic acid and ceto-stearyl alcohol.

Preferably component D is present at a level within the range 0.2 to 7 wt % based on the total composition.

Component E

As stated above, E is a material which comprises at least one of a compound selected from $3\beta$-sterol; squalane; squalene; saponins or sapogenins of the plant steroid or triterpenoid type; di and tri terpenes such as phytol, retinol and amyrin; and mixtures thereof. Potential sources of such material consist of wool wax alcohols (lanolin alcohols) and other alcoholic fractions of lanolin.

Preferably component E comprises a $3\beta$-sterol having a tail on the 17 position and having no polar groups, for example cholesterol, sitosterol, stigmasterol and ergosterol. Commercially available sources of cholesterol include Super Hartolan ex Croda which comprises at least 30% cholesterol.

Cholesterol is a vital component of the natural skin lipids constituting the moisture barrier in the stratum corneum.

Preferably component E is present at a level within the range 0.3 to 10 wt % based on the total composition.

The surface active agent can be selected from any known surfactant suitable for topical application to the human body. Mild surfactants, i.e. surfactants which do not damage the stratum corneum, the outer layer of skin, are particularly preferred.

One preferred anionic detergent is fatty acyl isethionate of formula:

$$RCO_2CH_2CH_2SO_3M$$

where R is an alkyl or alkanyl group of 7 to 21 carbon atoms and M is a solubilising cation such as sodium, potassium, ammonium or substituted ammonium. Preferably at least three quarters of the RCO groups have 12 to 18 carbon atoms and may be derived from coconut, palm or a coconut/palm blend.

Another preferred anionic detergent is alkyl ether sulphate of formula:

$$RO(CH_2CH_2O)_nSO_3M$$

where R is an alkyl group of 8 to 22 carbon atoms, n ranges from 0.5 to 10 especially 1.5 to 8, and M is a solubilising cation as before or $Mg^{2+}$.

Other possible anionic detergents include alkyl glyceryl ether sulphate, sulphosuccinates, taurates, sarconinates, sulphoacetates, alkyl phosphate, alkyl phosphate esters and acyl lactylate, alkyl glutamates, and mixtures thereof.

If the surface active agent comprises soap, the soap is preferably derived from materials with a $C_8$ to $C_{22}$ substantially saturated carbon chain and, preferably, is a potassium soap with a $C_{12}$ to $C_{18}$ carbon chain.

Sulphosuccinates may be monoalkyl sulphosuccinates having the formula: $R^5O_2CCH_2CH(SO_3M)CO_2M$; and amido-MEA sulphosuccinates of the formula: $R^5CONHCH_2CH_2O_2CCH_2CH(SO_3M)CO_2M$; wherein $R^5$ ranges from $C_8$–$C_{20}$ alkyl, preferably $C_{12}$–$C_{15}$ alkyl and M is a solubilising cation.

Sarcosinates are generally indicated by the formula: $R^5CON(CH_3)CH_2CO_2M$, wherein R ranges from $C_8$–$C_{20}$ alkyl, preferably $C_{12}$–$C_{15}$ alkyl and M is a solubilising cation.

Taurates are generally identified by the formula: $R^5CONR^6CH_2CH_2SO_3M$, wherein $R^5$ ranges from $C_8$–$C_{20}$ alkyl, preferably $C_{12}$–$C_{15}$ alkyl, $R^6$ ranges from $C_1$–$C_4$ alkyl, and M is a solubilising cation.

Harsh surfactants such as primary alkane sulphonate or alkyl benzene sulphonate will generally be avoided.

Suitable nonionic surface active agents include alkyl polysaccharides, lactobionamides, ethyleneglycol esters, glycerol monoethers, polyhydroxyamides (glucamide), primary and secondary alcohol ethoxylates, especially the $C_{8-20}$ aliphatic alcohols ethoxyloted with an average of from 1 to 20 moles of ethylene oxide per mole of alcohol.

Mixtures of any of the foregoing surface active agent may also be used.

The surface active agent is preferably present at a total level of from 1 to 45 wt %, preferably 3 to 30 wt %, and most preferably 5 to 20 wt %.

It is also preferable that the composition includes from 0.5 to 15 wt % of a cosurfactant agent with skin-mildness benefits. Suitable materials are zwitterionic detergents which have an alkyl or alkenyl group of 7 to 18 carbon atoms and comply with an overall structural formula

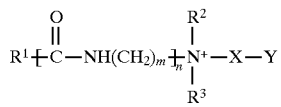

where $R^1$ is alkyl or alkenyl of 7 to 18 carbon atoms $R^2$ and $R^3$ are each independently alkyl, hydroxyalkyl or carboxyalkyl of 1 to 3 carbon atoms m is 2 to 4 n is 0 or 1

X is alkylene of 1 to 3 carbon atoms optionally substituted with hydroxyl, and

Y is $-CO_2^-$ or $-SO_3^-$

Zwitterionic detergents within the above general formula include simple betaines of formula:

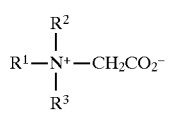

and amido betaines of formula:

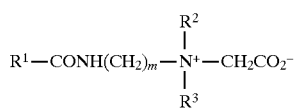

where m is 2 or 3.

In both formulae R$^1$, R$^2$ and R$^3$ are as defined previously. R$^1$ may, in particular be a mixture of C$_{12}$ and C$_{14}$ alkyl groups derived from coconut so that at least half, preferably at least three quarters of the groups R have 10 to 14 carbon atoms. R$^2$ and R$^3$ are preferably methyl.

A further possibility is a sulphobetaine of formula:

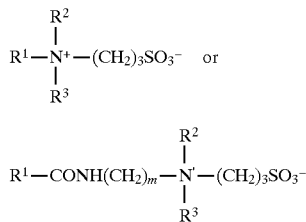

where m is 2 or 3, or variants of these in which -(CH$_2$)$_3$SO$_3$$^-$ is replaced by

R$^1$, R$^2$ and R$^3$ in these formulae are as defined previously.

Preferably the deposition aid is a cationic polymer prevent in an amount of at least 0.05% by weight of the total composition. It may well not exceed 3% or even 2% of the composition.

Various cationic polymers may be used. Examples of cationic polymers include the cationic cellulose others described in U.S. Pat. Nos. 3,816,616 and 4,272,515 and which are available commercially from Union Carbide Corp. under the trade mark POLYMER JR. Other suitable materials are the cationic polygalactomannan gum derivatives described in U.S. Pat. No. 4,298,494 which are commercially available under the trade mark JAGUAR. An example of a suitable material is the hydroxypropyltrimethylammonium derivative of guar gum of the formula:

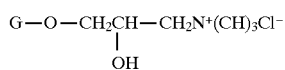

where G represents guar gum. Such a material is available under the name JAGUAR C-13-S. This material also has the CTFA designation Guar Hydroxypropyltrimonium Chloride. In JAGUAR C-13-S the degree of substitution of the cationic groups is about 0.13. Another possible material is that known as JAGUAR C-17 which is similar to JAGUAR C-13-S but has a higher degree of substitution of cationic groups of about 0.25–0.31. A further example of a guar derivative is the hydroxypropylated cationic guar derivative known as JAGUAR C-16 which as well as containing the above cationic quaternary ammonium groups also contain hydroxypropyl (-CH$_2$CH(OH)CH$_3$) substituent groups. In JAGUAR C-16 the degree of substitution of the cationic groups is 0.11–0.16 and the moles of substitution of hydroxypropyl groups is 0.8–1.1.

Other cationic polymers include cationic polyemides such as the low molecular weight adipic acid/diethylene-triamine polyamide and the copolymers of vinylpyrrolidone and dimethylaminoethyl methacrylate quaternised with dimethyl eulphate (Gafquat 755, GAF Corporation) described in U.S. Pat. No. 4,080,310; the graft cationic copolymer containing N-vinylpyrrolidone, dimethylaminoethyl methacrylate and polyethylene glycol described in U.S. Pat. No. 4,048,301; the mineral acid salts of the amino-alkyl eaters of homo- and copolymers of unsaturated carboxylic acids having from 3 to 5 carbon atoms described in U.S. Pat. No. 4,009,256, the polymers of etherified starch described in U.S. Pat. No. 3,186,911; and cationic polyacrylamides of the type described in International Patent Application WO95/22311.

The high molecular weight cationic polymers are sold under the trade mark MERQUAT by Merck & Co., Inc. Representative are Merquat 100, a highly charged cationic dimethyldiallylammonium chloride homopolymer, and Merquat (TM) 550, a highly charged Cationic copolymer prepared with dimethyldiallylammonium chloride and acrylamide. These materials are designated in the CTFA dictionary as Quaternium-40 and Quaternium-41, respectively.

Preferred cationic polymers include cationic cellulose ethers, cationic polygalactomannan gums and cationic polyacrylamides.

Other typical optional components which may be included in the compositions of the invention are humectants such as glycerol up to 10 wt %; opacifiers preferably at a level of 0.2 to 2.0 wt % preservatives, preferably 0.2 to 2.0 wt % and perfumes, preferably 0.5 to 3.0 wt %; bactericides; colourants; antioxidents; skin-feel modifiers; and thickeners and structurants such as swelling clays, cross-linked polyacrylates, for example, Carbopol (TM) (polymers available from Goodrich) and polyethoxypropylene glycoldioleate.

Compositions of the invention may be formulated as products for washing the skin, for example bath or shower gels; hand-washing compositions; facial washing liquids, and skin cleansers.

Without being bound by theory it is believed that the deposition aid assists deposition of the lipid composition onto the skin.

The composition of the invention is intended, during use, to reduce the permeability of the skin to water, particularly when the skin is dry or damaged, in order to reduce moisture loss and generally enhance the quality and flexibility of the skin.

In use, the composition is temporarily applied to the skin directly or by the use of an applicator. It is then removed from the skin such as by rinsing with water, particularly in the case of shower gels, or by wiping off such as with a tissue.

The composition according to the invention is preferably formulated as a liquid or gel having a viscosity in the range 1000 to 100 000 mPas measured at a shear rate of 10s$^{-1}$ and 25° C. in a Haake Rotoviscometer RV20.

Compositions according to the invention may be prepared by melting the components of the lipid composition. Water is then added to the resultant lipid melt. The surface active agent is melted and then added to the lipid/water mixture. The resultant mixture is cooled before cationic polymer and optional components are added.

The composition may be packaged in a suitable container from which it can be dispensed directly onto the skin or via an applicator. The invention accordingly provides a closed container containing the personal care composition as herein defined.

The invention also provides for the use in an aqueous liquid personal care composition which is temporarily applied to the skin of
   i) a lipid composition comprising two components D and E, where D is a molecule having one long hydrocarbon chain and a hydrophillic head group and E is a material which comprises at least one of a compound selected from 3β-sterol; squalane; squalene; saponins or sapogenins of the plant steroid or triterponoid type; di and tri terpenes such as phytol, retinol and amyrin; and mixtures thereof, wherein D and E are respectively present at levels within the range 0.1 to 10 wt % and 0.2 to 12 wt % based on the total composition;

ii) a surface active agent selected from anionic, nonionic, cationic, zwitterionic, amphoteric surface active agents, soap and mixtures thereof; and iii) a deposition aid; and the composition is substantially free of a molecule having at least two hydrocarbon chains and a polar head group which satisfies the relationship $$0.5 < \frac{V}{a_o l_c} \leq 1.0: \quad (I)$$

where

V is the volume of the hydrocarbon chains $I_c$ is the critical length of the hydrocarbon chains and $a_o$ is the optimum area of the polar head group.

The invention will now be further illustrated by reference to the non-limiting examples.

EXAMPLES

In the examples:

Lauric acid was Prifrac 2922 ex Unichema.

Myristic acid was Prifrac 2940.

Ethylene glycol monostearate was Empilan EGMS ex Albright & Wilson.

PEG 6000 distearate was Crothix ex Croda.

Cationic polymer was guar hydroxypropyl trimonium chloride was Jaguar C-13-S ex Meyhall except in example 2 where it was Jaguar C-14-S ex Meyhall.

Lanolin alcohol was Super Hartolan ex Croda containing at least 30% cholesterol.

Coco amidopropyl betaine (CAPB) was Tegobetaine C ex Goldschmidt.

Sodium lauryl ether oulphate (SLES) was Elfan NS 243S ex Akzo.

Stearic acid was Priscerine 4911.

Compositions according to the examples were prepared by melting the components of the lipid composition by heating to approximately 70° C. The lipid components were heated in glycerol when present in the formulations. Water was then added at approximately 70° C. In a separate vessel the surface active agents were heated to approximately 70° C. before being added sequentially to the molten lipid mixture. The resultant surface active agent/lipid mixture was mixed and mixing continued whilst it was cooled to room temperature. The cationic polymer, predispersed in perfume, was then added followed by minor components. Finally the pH of the composition was adjusted. This method may need minor modifications depending on the precise formulation.

Compositions formulated according to the invention and comparative compositions were tested by visual assessment of skin dryness and erythema of treated skins measurement of the reduction in water flux (TEWL) and measurement of the skin by a Corneometer.

The experimental procedure employed was as follows. This was carried out on human volunteers.

Both forearms of a human volunteer were washed with a commercially available toilet soap bar three times a day for 7 days. The forearms were wetted with warm water and the shower gel was dispensed directly onto the arm and then rubbed into a lather for 45 seconds. The forearms were then rinsed with warm water for 15 seconds before being patted dry. They were monitored for skin dryness and erythema on a daily basis.

On days 8–12 the volunteers forearms were washed with a composition formulated according to the invention or comparative formulations. (Formulations are given below). The forearms were wetted with warm water and the shower gel was dispensed directly onto the arm and then rubbed into a lather for 45 seconds. The forearms were then rinsed with warm water for 15 seconds before being patted dry. They were monitored for skin dryness and erythema on a daily basis. On day 13 only three washes were performed.

This test procedure can be used to assess the effectiveness of the compositions according to the invention in alleviating dryness produced during the first 7 days of the test.

A) Skin dryness and erythema

This was assessed visually and scored as below.

| Skin Dryness | Score |
| --- | --- |
| No visible dryness | 0 |
| Slightly white, barely perceptible | 1 |
| Moderate whiteness: | 2 |
| Slight patchy uplifting of skin | 3 |
| Sight uplifting of skin, uniform scaling | 4 |
| Erythema | Score |
| None | 0 |
| Barely perceptible | 0.25 |
| Slight | 0 |
| Mild/patchy | 1.0 |

B) Reduction in water flux (Trans Epidermal Water loss-TEWL)

TEWL measurements were carried out using a Servomed Evaporimeter EP1 on a fixed site on each of the volunteer's arms (arbitrarily set at 5 inches from the wrist). Measurements were taken i) prior to the start of trial;

ii) immediately prior to first wash on day 8; and iii) at least 1 hour after the last wash on day 13.

A Teflon probe, containing two sensors, was rested on the surface of the skin. These sensors measured the partial water vapour pressure at two distances above the skin surface. The read out from the equipment gave the rate of water evaporation from the skin surface.

C) Corneometer readings

Corneometer readings were taken at the same time as the TEWL readings. The procedure involved resting a conductance probe on the skin surface for a few seconds. The value obtained provided a measure of the hydration state of the outer layer of skin.

D) Amount of lipid deposited onto skin

The following method was used to determine the amount of lipid deposited onto the skin of a human volunteer after it had been washed with the compositions according to the invention was determined.

The volunteers washed their forearms with a shower gel. The procedure involved wetting the arm and also the volunteer's free hand with warm water then using the free hand to lather the arm with 0.5 ml of a formulation for 10 seconds, next rinsing for 10 seconds while rubbing with the free hand and then drying the arm with a single pass with a paper towel.

10 minutes after drying the forearm a glass cylinder was applied to two areas of skin on the forearm. The skin enclosed by the cylinder (10 cm$^2$) was extracted three times with 1 ml of ethanol. The amount of cholesterol in the extract was determined using an enzymatic kit from Sigma (352-20). This procedure was repeated for each of the formulations to be tested.

EXAMPLE 1

The following formulations ware prepared and tested.

TABLE I

| Formulation | % by weight | | |
|---|---|---|---|
| | I | C1 | C2 |
| SLES | 16.0 | 16.0 | 16.0 |
| CAPB | 2.0 | 2.0 | 2.0 |
| Lanolin alcohol | 2.50 | — | 2.5 |
| Stearic Acid | 1.25 | — | — |
| Cationic polymer | 0.25 | 0.25 | 0.25 |
| Glycerol | 5.00 | 5.00 | 5.00 |
| Water + preservatives + minors ← to 100 → | | | |

The following results were obtained.

TABLE II

| FORMULATION | I | C1 | Statistical Significance |
|---|---|---|---|
| DRYNESS | | | |
| Day 8 | 2.92 | 2.77 | |
| Day 13 | 2.33 | 1.90 | $p = <0.05$ |
| TEWL/g/m$^2$/h | | | |
| Day 8 | 6.80 | 7.66 | |
| Day 13 | 8.03 | 7.15 | $p = <0.05$ |
| HYDRATION (CORNEOMETER) | | | |
| Day 8 | 63.21 | 61.77 | |
| Day 13 | 58.23 | 63.97 | $p = <0.05$ |
| n | | 21 | | n is the number of volunteers who took part in the test.

The results demonstrate the clinical benefit for a composition comprising a binary lipid system in terms of dryness, hydration and water barrier properties of skin treated therewith.

For test D the following results were obtained:

| Formulation | Cholesterol ($\mu$g/10cm$^3$) |
|---|---|
| I | 13.54 |
| C1 | 8.19 |
| C2 | 11.78 |

The results demonstrate that when both lipid components are present in the composition there is an increase in the level of lipid deposited compared to that found when the compositions contain only one of the lipid components.

EXAMPLE 2

In this example formulation II, according to the invention, and comparative formulation C3 were each independently compared against a commercially available mild surfactant facial wash product (C4). Twenty panellists were used in this test.

TABLE III

| Component | II | C3 |
|---|---|---|
| SLES | 12.0 | 12.0 |
| CAPB | 7.5 | 7.5 |
| Glycerol | 5.0 | 5.0 |
| PEG4000 | 5.0 | 5.0 |
| Clay | 1.5 | 1.5 |
| Lanolin alcohol | 2.5 | 2.5 |
| Cetostearyl alcohol | 1.25 | — |
| Opacifier | 0.4 | 0.4 |
| Isopropyl palmitate | 0.5 | 0.5 |
| Cationic polymer | 0.25 | 0.25 |
| Perfume + minors + water | ← to 100 → | |

The following results were obtained.

TABLE IV

| DRYNESS | II | C4 | Statistical Significance |
|---|---|---|---|
| Day 8 | 2.45 | 2.40 | |
| Day 13 | 1.45 | 1.85 | $p = 0.06$ |
| DRYNESS | C3 | C4 | |
| Day 8 | 2.60 | 2.70 | |
| Day 13 | 1.80 | 1.95 | $p = 0.49$ (NS) |

The results demonstrate that a composition containing only one of the lipid components, namely component E, is ineffective compared to a system containing both lipid components D and E.

EXAMPLE 3

In this example formulations III and IV according to the invention were compared against a system from which lipid component E was absent. (Formulation C5). 8 panellists took part in this test.

TABLE V

| Formulation | III | IV | C5 |
|---|---|---|---|
| | wt % | | |
| Lauric Acid | 7.69 | 7.96 | 7.69 |
| Myristic Acid | 7.69 | 7.69 | 7.69 |
| Stearic Acid | 9.62 | 9.62 | 9.62 |
| Ethylene Glycol Monostearate | 6.00 | 6.00 | 6.00 |
| PEG 6000 Distearate | 2.00 | 2.00 | 2.00 |
| Propan-1,2-diol | 5.00 | 5.00 | 5.00 |
| Glycerol | 13.00 | 13.00 | 13.00 |
| Potassium Hydroxide* | — | — | — |
| Cationic Guar Gum | 0.10 | 0.10 | 0.10 |
| Lanolin Alcohols | 1.50 | 3.00 | — |
| Perfume and minors | ← to 100 → | | |

*Adjusted to a level to ensure that the fatty acids will not be fully saponified giving a level of free fatty acid of at least 0.2 wt %.

The following results were obtained:

TABLE VI

| Formulation | Cholesterol ($\mu$g/10cm$^3$) |
|---|---|
| III | 5.021 |
| IV | 5.068 |
| C5 | 3.621 |

The results demonstrate that cholesterol is deposited from a fatty acid soap based system personal care composition containing lanolin alcohol.

We claim:

1. A personal wash composition in the form of an aqueous liquid comprising:
   (i) a lipid composition comprising two components D and E;
   wherein D is selected from the group consisting of stearic acid and cetostearyl alcohol;
   wherein E is selected from the group consisting of cholesterol, sitosterol, stigmosterol and ergosterol; and
   wherein D & E are respectively present at levels within the range 0.1 to 10 wt. % and 0.2 to 12 wt. % based on the total composition;
   (ii) a surface active agent selected from the group consisting of anionic, nonionic, cationic, zwitterionic, amphoteric surface active agents, soap and mixtures thereof; and
   (iii) a cationic polymer selected from the group consisting of cationic cellulose ethers, cationic polygalactomannan gums, cationic polyacrylamides and mixtures thereof; and
   the composition is substantially free of a molecule having at least two hydrocarbon chains and a polar head group which satisfies the relationship $$0.5 < \frac{V}{a_o I_c} \leq 1.0: \quad (I)$$

where
V is the volume of the hydrocarbon chains
$I_c$ is the critical length of the hydrocarbon chains and
$a_o$ is the optimum area of the polar head group.

* * * * *